US007228725B2

(12) United States Patent
Salter et al.

(10) Patent No.: US 7,228,725 B2
(45) Date of Patent: Jun. 12, 2007

(54) THIN FILM GAS SENSOR CONFIGURATION

(75) Inventors: Carlton Salter, Stevenson Ranch, CA (US); Robert Pendergrass, Saugus, CA (US)

(73) Assignee: H2scan LLC, Valencia, CA (US)

( * ) Notice: Subject to any disclaimer, the term of this patent is extended or adjusted under 35 U.S.C. 154(b) by 40 days.

(21) Appl. No.: 11/046,370

(22) Filed: Jan. 27, 2005

(65) Prior Publication Data
US 2005/0183967 A1    Aug. 25, 2005

Related U.S. Application Data

(60) Provisional application No. 60/540,020, filed on Jan. 27, 2004.

(51) Int. Cl.
*G01N 7/00* (2006.01)
*G01N 25/00* (2006.01)

(52) U.S. Cl. ..................... 73/31.05; 73/25.05
(58) Field of Classification Search .............. 73/25.05, 73/31.05, 31.06; 257/253
See application file for complete search history.

(56) References Cited

U.S. PATENT DOCUMENTS

| 3,674,436 | A |   | 7/1972  | Geul            |          |
|-----------|---|---|---------|-----------------|----------|
| 4,654,624 | A |   | 3/1987  | Hagan et al.    |          |
| 4,984,446 | A | * | 1/1991  | Yagawara et al. | 73/31.06 |
| 5,003,812 | A | * | 4/1991  | Yagawara et al. | 73/31.06 |
| 5,012,671 | A | * | 5/1991  | Yagawara et al. | 73/31.06 |
| 5,071,770 | A | * | 12/1991 | Kolesar, Jr.    | 436/151  |
| 5,279,795 | A |   | 1/1994  | Hughes et al.   |          |
| 5,777,207 | A | * | 7/1998  | Yun et al.      | 73/31.05 |
| 6,786,076 | B2 | * | 9/2004 | Raisanen       | 73/31.05 |
| 6,906,392 | B2 | * | 6/2005 | Benzel et al.  | 257/414  |

FOREIGN PATENT DOCUMENTS

| JP | 6486052       | * | 3/1989 |
| WO | WO-01/36961 A  |   | 5/2001 |
| WO | WO 01/36961 A1 |   | 5/2001 |

OTHER PUBLICATIONS

Hughes, Robert C. et al., "Sensors for Detecting Molecular Hydrogen Based on Pd Metal Alloys", Sandia National Laboratories, Microsensor Research and Development Department, Albuquerque, NM, 1997.
W L Gore & Associates, "Gore™ Membrane Vents, Series HPM: High Protection Against Metal Impact" Product Data Sheet, 2002.

* cited by examiner

*Primary Examiner*—Michael Cygan
(74) *Attorney, Agent, or Firm*—McAndrews, Held & Malloy, Ltd.

(57) ABSTRACT

A gas sensor for sensing a gas stream constituent includes, mounted a substrate, a first gas-sensing element capable of sensing the constituent in a first concentration range, a reference element insensitive to the constituent and having electrical properties congruent with the first gas-sensing element, a heating element substantially circumscribing the first gas-sensing element and the reference element, a temperature-sensing element circumscribing the first gas-sensing element and the reference element, and a second gas-sensing element capable of sensing the constituent in a second concentration range. The first gas-sensing element and the reference element are preferably metal-gated metal-oxide semiconductor (MOS) solid-state devices. The gas sensor is particularly configured to sense hydrogen concentration in a gas stream.

7 Claims, 3 Drawing Sheets

THIN FILM GAS SENSOR CONFIGURATION

CROSS-REFERENCE TO RELATED APPLICATION(S)

This application is related to and claims priority benefits from U.S. Provisional Patent Application Ser. No. 60/540,020, filed on Jan. 27, 2004. The '020 provisional application is hereby incorporated by reference herein in its entirety.

FIELD OF THE INVENTION

The present invention relates to sensors for detecting the presence of a constituent in a gaseous stream. More particularly, the present invention relates to a hydrogen gas sensor configuration having first and second hydrogen sensing elements, a reference element, a heating element, and a temperature-sensing element.

BACKGROUND OF THE INVENTION

In gas sensor applications, the arrangement of the sensor elements on their underlying substrate should exhibit certain attributes to improve or optimize their performance. In particular, it is desirable to physically arrange and integrate the sensing and operational elements of the sensor so that the components are maintained at essentially the same temperature. In practice, the sensor elements should be arranged so as to minimize the substrate area occupied by the elements, thereby reducing or minimizing thermal convection and conduction losses among the sensor elements. Secondarily, minimizing the occupied substrate area also reduces the amount of substrate material required to fabricate the sensor, and thus reduces fabricating costs.

Conventional, prior art solutions, such as those developed at Sandia National Laboratories (see R. Thomas and R. Hughes, "Sensors for Detecting Molecular Hydrogen Based on PD Metal Alloys", *J. Electrochem. Soc.*, Vol. 144, No. 9, September 1997; and U.S. Pat. No. 5,279,795), involve the interlacing of the sensing and operational elements of the sensor. Such conventional solutions employ a geometry that deploys the sensor elements over a significantly larger area than necessary, thus rendering the design less effective in terms of thermal layout, in that the sensing element(s) of the sensor (capacitive metal-on-silicon (MOS) elements in the case of the Sandia design) do not occupy a common, uniform thermal environment. The Sandia design also has greater than optimal manufacturing costs due to the interlaced design rendering unused significant portions of the underlying substrate material. The Sandia and similar prior art designs did not seek to optimize the thermal environment of the sensor assembly. Nor did the Sandia or similar prior art designs seek to optimize the mechanical compactness of the sensor assembly.

Although conventional, prior art solutions had some thermal integration of the heating element, the temperature sensor and the gas sensor, the geometry was such that these elements could become flow sensitive. Flow sensitivity refers to the effect that the flow rate of the gas stream to be measured can have in conducting heat from the element(s), thereby lowering their temperature and requiring additional electrical power to restore the temperature of the element(s) to their original and desired level. Sandia-type sensor designs included an additional capacitive (MOS) sensor, which was located outside of the portion of the assembly having controllable and uniform thermal properties. Moreover, such conventional, prior art designs had considerable wasted space on the underlying silicon die or substrate on which the sensor elements were arranged, which would multiply (approximately triple) the manufacturing costs and heat loss from the sensor elements to the external environment.

In the present gas sensor assembly, the sensing and control elements are mounted on the underlying substrate and operated so as to maintain thermal integrity and prevent heat loss. In particular, the area occupied by the sensor elements is minimized or conserved to minimize or reduce thermal losses to convection/conduction of heat to and from the sensor components. The present gas sensor assembly is also configured for compactness to minimize or reduce manufacturing and parts costs by maximizing or increasing the number of sensor elements mounted on a substrate.

SUMMARY OF THE INVENTION

One or more of the foregoing shortcomings of conventional, prior art gas sensors is overcome by the present gas sensor, which integrates four thin-film elements in a geometric configuration that conserves and/or optimizes the area occupied on a die substrate, while reducing and/or minimizing thermal heat losses.

The present gas sensor for sensing a gas stream constituent comprises:
 (a) a thermally conductive, electrically insulative substrate;
 (b) a first gas-sensing element mounted on the substrate, the first gas-sensing element capable of sensing the constituent in a first concentration range;
 (c) a reference element mounted on the substrate, the reference element and the first gas-sensing element having congruent electrical properties, the reference element insensitive to the constituent;
 (d) a heating element mounted on the substrate and substantially circumscribing the first gas-sensing element and the reference element;
 (e) a temperature-sensing element mounted on the substrate and substantially circumscribing the first gas-sensing element and the reference element;
 (f) a second gas-sensing element mounted on the substrate capable of sensing the constituent in a second concentration range.

In a preferred embodiment of the present gas sensor, each of the first gas-sensing element and the reference element comprises a material having electrical properties that change upon exposure to the gas stream constituent. The temperature-sensing element preferably substantially circumscribes the heating element. The second gas-sensing element preferably substantially circumscribes the first gas-sensing element and the reference element. The second gas-sensing element preferably substantially circumscribes the temperature-sensing element.

In a preferred embodiment of the present gas sensor, each of the first gas-sensing element and the reference element is a metal-gated metal-oxide semiconductor (MOS) solid-state device. The MOS device can comprise a MOS capacitor. The MOS device can also comprise a MOS transistor. The metal gate of the first gas-sensing MOS device preferably comprises a metal selected from the group consisting of palladium and a palladium alloy. The palladium alloy is preferably selected from the group consisting of palladium/nickel, palladium/gold and palladium/silver. The metal gate of the reference element MOS device preferably comprises a metal that is inert with respect to the gas stream constituent. The preferred inert metal is gold. The metal gate of the reference element MOS device can also comprise a passivated metal that is non-inert with respect to the gas stream constituent. The non-inert metal is preferably passivated by application of an inert coating material, such as glass or an inert polymeric material.

In a preferred embodiment of the present gas sensor, the substrate comprises a silicon-containing material. The heating element is preferably a resistive heating element. The temperature-sensing element preferably comprises a material having a stable temperature coefficient of resistance, most preferably nickel. The second gas-sensing element is preferably a catalytic metal resistor, most preferably a palladium/nickel alloy.

The present gas sensor is particularly configured to sense hydrogen concentration in a gas stream The first gas-sensing element senses hydrogen in a first concentration range of from $10^{-6}$ Torr to 10 Torr. The second gas-sensing element senses hydrogen in a second concentration range of greater than 1 Torr.

A method of sensing a gas stream constituent comprises:
(a) sensing the constituent in a first concentration range by measuring a voltage difference between a first gas-sensing element mounted on a substrate and a reference element mounted on the substrate, the reference element and the first gas-sensing element having congruent electrical properties, the reference element insensitive to the constituent; and
(b) sensing the constituent in a second concentration range by measuring a change in electrical properties of a second gas-sensing element mounted on the substrate.

A preferred embodiment of the sensing method further comprises:
(c) maintaining the first gas-sensing element and the reference element in a uniform temperature environment.

The uniform temperature environment is preferably maintained using a heating element that is responsive to a temperature-sensing element, the heating element substantially circumscribing the first gas-sensing element and the reference element, and the temperature-sensing element substantially circumscribing the first gas-sensing element, the reference element and the heating element.

A method of fabricating a gas sensor for sensing a gas stream constituent, the fabricating method comprises:
(a) mounting a first gas-sensing element on a thermally conductive, electrically insulative substrate, the first gas-sensing element capable of sensing the constituent in a first concentration range;
(b) mounting a reference element on the substrate, the reference element and the first gas-sensing element having congruent electrical properties, the reference element insensitive to the constituent;
(c) mounting a heating element on the substrate such that the heating element substantially circumscribes the first gas-sensing element and the reference element;
(d) mounting a temperature-sensing element on the substrate such that the temperature-sensing element substantially circumscribes the first gas-sensing element and the reference element; and
(e) mounting a second gas-sensing element on the substrate, the second gas-sensing element capable of sensing the constituent in a second concentration range.

In the preferred fabricating method, each of the first gas-sensing element and the reference element comprises a material having electrical properties that change upon exposure to the gas stream constituent. The temperature-sensing element preferably substantially circumscribes the heating element. The second gas-sensing element preferably substantially circumscribes the first gas-sensing element and the reference element. The second gas-sensing element more preferably substantially circumscribes the temperature-sensing element. Each of the first gas-sensing element and the reference element is preferably a metal-gated metal-oxide semiconductor (MOS) solid-state device. The MOS device can comprise a MOS capacitor and can also comprise a MOS transistor.

BRIEF DESCRIPTION OF THE DRAWING(S)

DETAILED DESCRIPTION OF PREFERRED EMBODIMENT(S)

The principal improvement achieved by the present thin film gas sensor design is that of employing a compact, thermally efficient design that has geometrical symmetry and surrounds that geometry with heating and sensing elements. The geometry is regular to minimize or reduce unused die surface area. The compact configuration minimizes or reduces sensitivity to temperature differences across the surface area of the sensor, both by virtue of the integrated geometry and the compact geometry.

Figure 1:
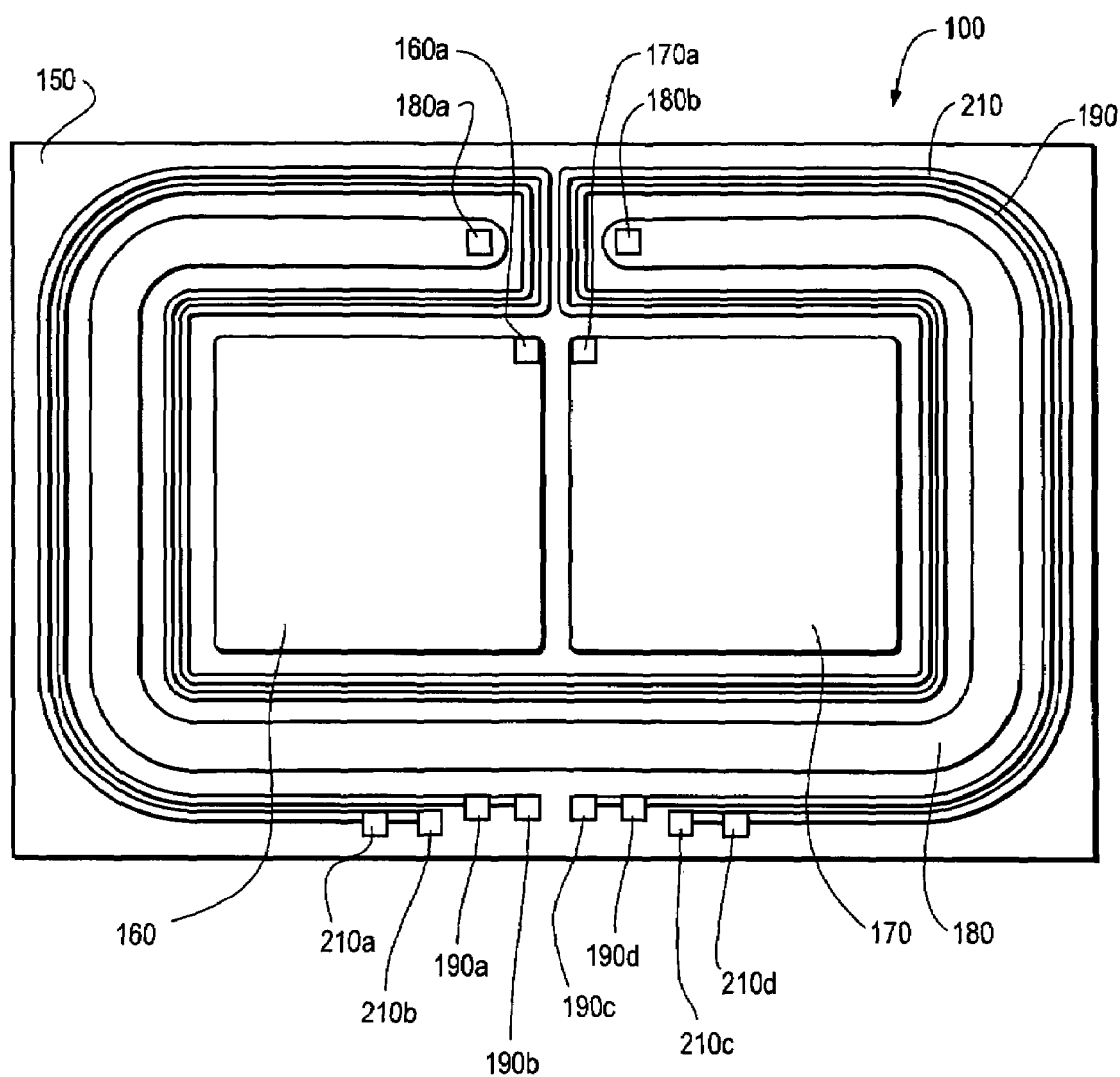
FIG. 1 is a schematic diagram showing the present thin film gas sensor in plan view.

Turning to FIG. 1, a thin film gas sensor 100 is capable of sensing a constituent (hydrogen in the device depicted in the figures and described in detail below) in a gas stream directed across gas sensor 100. Sensor 100 includes a thermally conductive, electrically insulative substrate 150. Substrate 150 preferably comprises a silicon-containing material. A first gas-sensing element 160 is mounted on substrate 150. The first gas-sensing element capable of sensing the constituent in a first concentration range.

As further shown in FIG. 1, a reference element 170 is mounted on the substrate. While first gas-sensing element 160 is sensitive to hydrogen, reference element 170 is insensitive to hydrogen. However, reference element 170 and first gas-sensing element 160 have congruent electrical properties (that is the electrical properties of reference element 170, if rendered sensitive to hydrogen, would exhibit changes in voltage and/or resistance corresponding to the changes in voltage and/or resistance exhibited by first gas-sensing element 160).

A heating element 180 is mounted on substrate 150, and substantially circumscribes first gas-sensing element 160 and reference element 170, as shown in FIG. 1. A temperature-sensing element 190 is also mounted on substrate 150 and substantially circumscribes first gas-sensing element 160 and reference element 170. In the illustrated configuration, temperature-sensing element 190 also substantially circumscribes heating element 180.

A second gas-sensing element 210 is also mounted on substrate 150. In the illustrated configuration, second gas-sensing element 210 substantially circumscribes first gas-sensing element 160 and reference element 170, and also substantially circumscribes temperature-sensing element 190. Second gas-sensing element 210 shown in FIG. 1 is a catalytic metal resistor, preferably formed from a palladium/nickel alloy, and is capable of sensing hydrogen in a second concentration range.

First gas-sensing element 160 and reference element 170 are preferably metal-on-silicon (MOS) capacitors. Such MOS devices are not restricted to a capacitive form, however, but could be implemented in p-n-p transistor, field-effect transistor (FET) or diode configurations as well.

In gas sensor 100 illustrated in FIG. 1, each of first gas-sensing element 160 and reference element 170 is a metal-gated metal-oxide semiconductor (MOS) solid-state capacitive device. The metal gate of first gas-sensing element 160 is preferably formed from palladium/nickel. The metal gate of the reference element 170 is preferably formed from gold. Heating element 180 shown in FIG. 1 is a resistive heating element. Temperature-sensing element 190 shown in FIG. 1 is preferably formed from nickel. Second gas-sensing element 210 is a catalytic metal resistor, preferably formed from a palladium/nickel alloy.

As shown in FIG. 1, first gas-sensing element 160 has a terminal 160a formed therein. Reference element 170 has a terminal 170a formed therein. Heating element 180 has a pair of terminals 180a, 180b formed therein at opposite ends of its trace on substrate 150. Temperature-sensing element 190 has two pairs of terminals 190a, 190b and 190c, 190d formed therein at opposite ends, respectively, of its trace on substrate 150. Second gas-sensing element 210 also has two pairs of terminals 210a, 210b and 210c, 290d formed therein at opposite ends, respectively, of its trace on substrate 150.

Figure 2:
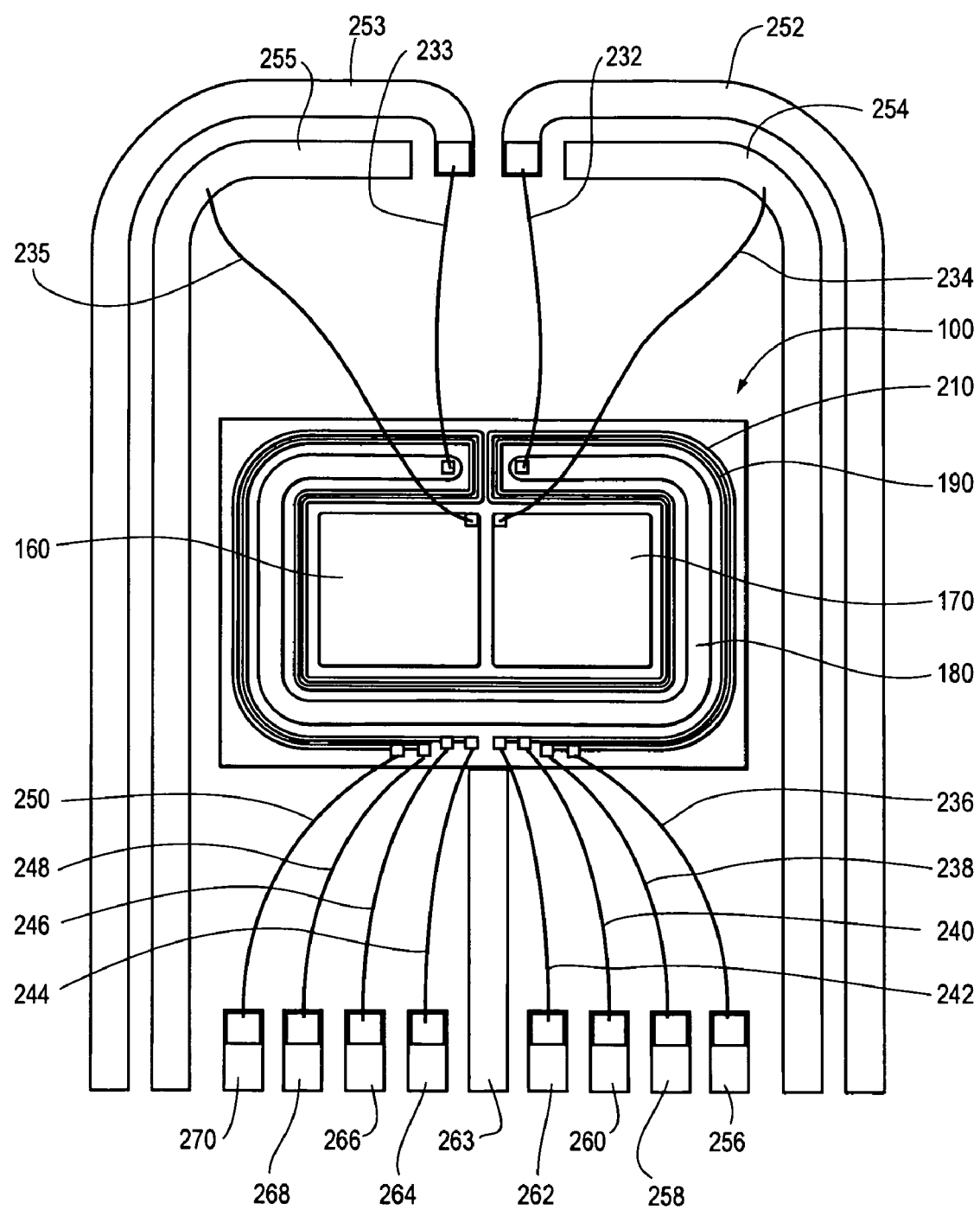
FIG. 2 is an enlarged view of the proximal end of a flexible circuit that incorporates the gas sensor of FIG. 1.
Figure 3:
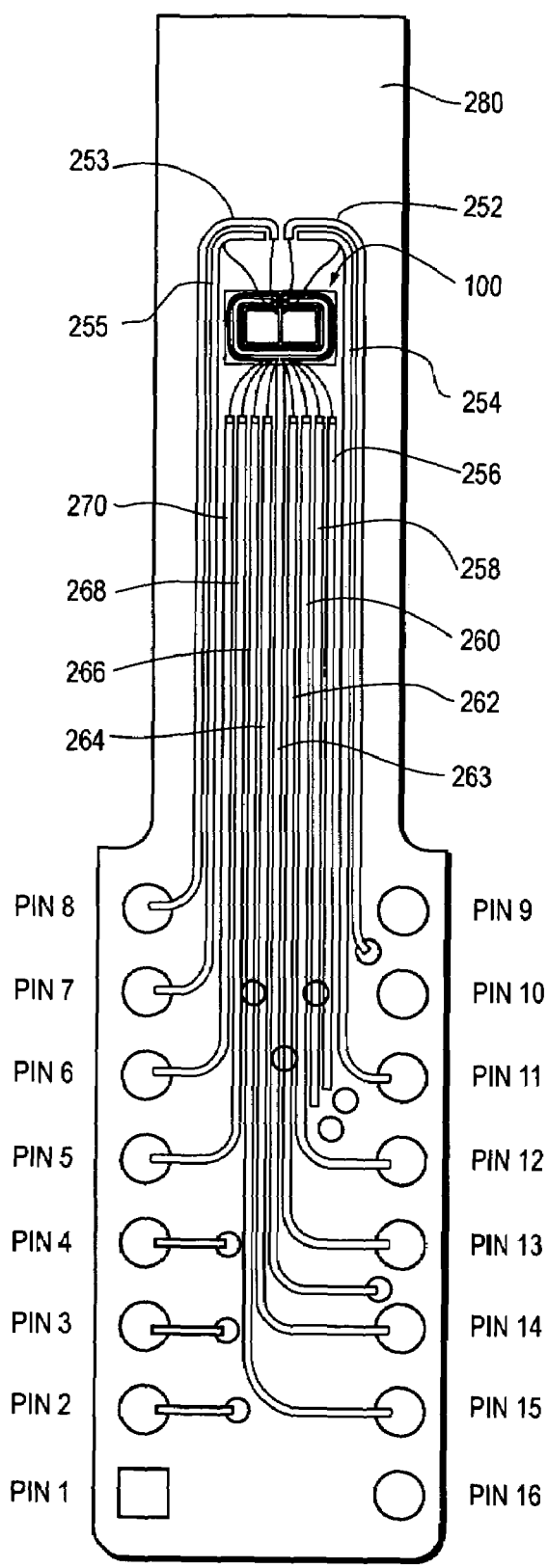
FIG. 3 shows in plan view the gas sensor of FIG. 1 incorporated at the distal end of a flexible circuit having pin connections at its proximal end, which extend from the flexible for mounting on a circuit board.

FIG. 2 is an enlarged view of the proximal end of a flexible circuit (shown as flex circuit 280 in FIG. 3) that incorporates gas sensor 100 of FIG. 1. FIG. 2 shows in detail the electrical connections between gas sensor 100 and the flex circuit. The flex circuit has a plurality of copper traces disposed on its upper surface. As illustrated in FIG. 3 and described in the text below accompanying FIG. 3, the copper traces at the distal end of the flex circuit extend to and are electrically connected to pin connections, located at the proximal end of flex circuit, for mounting on a circuit board (not shown).

As shown in FIG. 2, sensor 100 includes substrate 150, on which are mounted first gas-sensing element 160, reference element 170, heating element 180, temperature-sensing element 190 and second gas-sensing element. As further shown in FIG. 2, bond wire 235 connects first gas-sensing element 160 to copper trace 255. Bond wire 234 connects reference element 170 to copper trace 254. Bond wires 232, 233 connect heating element 180 to copper traces 252, 253, respectively. Two pairs of bond wires 240, 242 and 248, 250 connect temperature-sensing element 190 to copper traces 260, 262 and 268, 270, respectively. Similarly, two pairs of bond wires 236, 238 and 244, 246 connect second gas-sensing element 210 to copper traces 256, 258 and 264, 266, respectively. Substrate 150 is electrically connected to copper trace 263.

FIG. 3 shows gas sensor 100 incorporated at the distal end of flex circuit 280, which has pin connections PIN 1 through PIN 16 at its proximal end for mounting on a circuit board (not shown in FIG. 3). For simplicity and ease of interpretation, FIG. 3 shows only the connections of the copper traces to the pin connections. Thus, although the wire connections at the proximal end of flex circuit 280 are not shown, persons skilled in the technology involved here will recognize that the proximal end wire connections omitted from FIG. 3 can be readily configured using ordinary circuit design techniques.

As shown in FIG. 3, the proximal end of trace 252 terminates at a terminal other than a pin connection, from which it is electrically connected by a wire (not shown) to another terminal or pin. The proximal end of trace 253 terminates at PIN 8. The proximal end of trace 254 terminates at PIN 11. The proximal end of trace 255 terminates at PIN 7. The proximal end of trace 256, 258 terminate at adjacent terminals other than a pin connection, from which they are electrically connected by wires (not shown) to other terminal(s) or pin(s). The proximal end of trace 260 terminates at PIN 12. The proximal end of trace 262 terminates at PIN 13. The proximal end of trace 263 terminates at an adjacent terminal other than a pin connection, from which it is electrically connected by a wire (not shown) to another terminal or pin. The proximal end of trace 264 terminates at PIN 14. The proximal end of trace 266 terminates at PIN 15. The proximal end of trace 268 terminates at PIN 5. The proximal end of trace 270 terminates at PIN 6. PIN 2, PIN 3 and PIN 4 are electrically connected by copper traces to terminal other than a pin connection, from which it is electrically connected by a wire (not shown) to other terminal(s) or pin(s). PIN 1 and PIN 16 are not connected to traces emanating from gas sensor 100. Each of PIN 1 through PIN 16 extends downwardly through flex circuit and are insertable into aligned mounting holes in a circuit board (not shown), which contains the downstream processing and control circuitry to which the signals from flex circuit 280 are directed.

Figure 4:
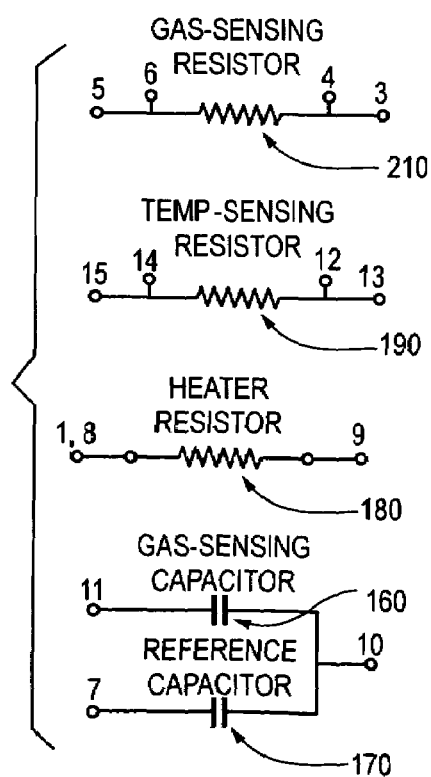
FIG. 4 is a schematic circuit diagram identifying the pin connections for each of the gas sensor elements illustrated in FIG. 3.

FIG. 4 is a schematic circuit diagram identifying the pin connections for each of the gas sensor elements. Gas-sensing capacitor 160 is connected at one end to PIN 11 and at its other end to PIN 10. Reference capacitor 170 is connected at one end to PIN 7 and at its other end to PIN 10. Heater resistor 180 is connected at one end to PIN 1 and PIN 8 and at its other end to PIN 9. Temperature-sensing resistor 190 is connected at one end to PIN 14 and PIN 15 and at its other end to PIN 12 and PIN 13. Gas-sensing resistor 210 is connected at one end to PIN 5 and PIN 6 and at its other end to PIN 3 and PIN 4.

The integrated die sensor assembly has been tested and has been shown to maintain favorable functional isolation among the sensing elements, exhibits reduced flow sensitivity, is thermally responsive, and is easily manufactured.

The advantages are the present thin film gas sensor include:

(a) rapid temperature response due the minimization of die area and thereby mass;

(b) reduced sensitivity to gas stream flow;

(c) effective thermal coupling among the sensor and control elements;

(d) ease of manufacture; and (e) ease of packaging onto either standard dual in-line packages or flex harness.

Although the present device has been implemented in its preferred embodiment to sense hydrogen, persons skilled in the technology involved here will recognize that one or more aspects of the present device could be implemented or readily modified to sense and/or detect the presence and/or amount of constituents in fluid streams generally, including gas streams containing hydrogen and/or other than hydrogen, liquid streams, liquid streams containing entrained gas(es) and/or solid(s), gas streams containing entrained liquid(s) and/or solid(s). Moreover, aspects of the present device could be implemented or readily modified to sense and/or detect the presence and amount of fluid constituents residing in the pores and/or lattice structure of solids.

While particular steps, elements, embodiments and applications of the present invention have been shown and described, it will be understood, of course, that the invention is not limited thereto since modifications can be made by those skilled in the art, particularly in light of the foregoing teachings.

What is claimed is:

1. A gas sensor for sensing a gas stream constituent, the gas sensor comprising:
   (a) a thermally conductive, electrically insulative substrate;
   (b) a first gas-sensing element mounted on said substrate, said first gas-sensing element capable of sensing said constituent in a first concentration range;
   (c) a reference element mounted on said substrate, said reference element and said first gas-sensing element having congruent electrical properties, said reference element insensitive to said constituent;
   (d) a heating element mounted on said substrate and substantially circumscribing said first gas-sensing element and said reference
   (e) a temperature-sensing element mounted on said substrate and substantially circumscribing said first gas-sensing element and said reference element;
   (f) a second gas-sensing element mounted on said substrate capable of sensing said constituent in a second concentration range such that said heating element imparts at least some convective heat to said second gas-sensing element;
   wherein said temperature-sensing element substantially circumscribes said heating element.

2. A gas sensor for sensing a gas stream constituent, the gas sensor comprising:
   (a) thermally conductive, electrically insulative substrate;
   (b) a first gas-sensing element mounted on said substrate, said first gas-sensing element capable of sensing said constituent in a first concentration range;
   (c) a reference element mounted on said substrate, said reference element and said first gas-sensing element having congruent electrical properties, said reference element insensitive to said constituent;
   (d) a heating element mounted on said substrate and substantially circumscribing said first gas-sensing element and said reference element;
   (e) a temperature-sensing element mounted on said substrate and substantially circumscribing said first gas-sensing element and said reference element;
   (f) a second gas-sensing element mounted on said substrate capable of sensing said constituent in a second concentration range such that said heating element imparts at least some convective heat to said second gas-sensing element, and wherein said second gas-sensing element substantially circumscribes said first gas-sensing element and said reference element.

3. The gas sensor of claim 2 wherein said second gas-sensing element substantially circumscribes said temperature-sensing element.

4. A method of sensing a gas stream constituent comprising:
   (a) sensing said constituent in a first concentration range by measuring a voltage difference between a first gas-sensing element mounted on a substrate and a reference element mounted on said substrate, said reference element and said first gas-sensing element having congruent electrical properties, said reference element insensitive to said constituent;
   (b) sensing said constituent in a second concentration range by measuring a change in electrical properties of a second gas-sensing element mounted on said substrate;
   (c) maintaining said first gas-sensing element, said second gas-sensing element, and said reference element in a uniform temperature environment, wherein said uniform temperature environment is maintained using a heating element that is responsive to a temperature-sensing element, said heating element substantially circumscribing said first gas-sensing element and said reference element, and said temperature-sensing element substantially circumscribing said first gas-sensing element, said reference element and said heating element.

5. A method of fabricating a gas sensor for sensing a gas stream constituent, the fabricating method comprising:
   (a) mounting a first gas-sensing element on a thermally conductive, electrically insulative substrate, said first gas-sensing element capable of sensing said constituent in a first concentration range;
   (b) mounting a reference element on said substrate, said reference element and said first gas-sensing element having congruent electrical properties, said reference element insensitive to said constituent;
   (c) mounting a heating element on said substrate such that said heating element substantially circumscribes said first gas-sensing element and said reference element;
   (d) mounting a temperature-sensing element on said substrate such that said temperature-sensing element substantially circumscribes said first gas-sensing element and said reference element;
   (e) mounting a second gas-sensing element on said substrate, said second gas-sensing element capable of sensing said constituent in a second concentration range, such that at least some convective heat from said heating element is imparted to said second gas-sensing element;
   wherein said temperature-sensing element substantially circumscribes said heating element.

6. A method of fabricating a gas sensor for sensing a gas stream constituent, the fabricating method comprising:
   (a) mounting a first gas-sensing element on a thermally conductive, electrically insulative substrate, said first gas-sensing element capable of sensing said constituent in a first concentration range;
   (b) mounting a reference element on said substrate, said reference element and said first gas-sensing element having congruent electrical properties, said reference element insensitive to said constituent;
   (c) mounting a heating element on said substrate such that said heating element substantially circumscribes said first gas-sensing element and said reference element;
   (d) mounting a temperature-sensing element on said substrate such that said temperature-sensing element substantially circumscribes said first gas-sensing element and said reference element;
   (e) mounting a second gas-sensing element on said substrate, said second gas-sensing element capable of sensing said constituent in a second concentration range, such that at least some convective heat from said heating element is imparted to said second gas-sensing element;
   wherein said second gas-sensing element substantially circumscribes said first gas-sensing element and said reference element.

7. The fabricating method of claim 6 wherein said second gas-sensing element substantially circumscribes said temperature- sensing element.

* * * * *